United States Patent

Sano et al.

Patent Number: 5,529,712
Date of Patent: Jun. 25, 1996

[54] DETERGENT COMPOSITION

[75] Inventors: Keigo Sano; Tatsuya Hattori, both of Kawasaki, Japan

[73] Assignee: Ajinomoto Co., Inc., Tokyo, Japan

[21] Appl. No.: 338,520

[22] PCT Filed: Mar. 30, 1994

[86] PCT No.: PCT/JP94/00514

§ 371 Date: Jan. 12, 1995

§ 102(e) Date: Jan. 12, 1995

[87] PCT Pub. No.: WO94/22994

PCT Pub. Date: Oct. 13, 1994

[30] Foreign Application Priority Data

Mar. 30, 1993 [JP] Japan .................... 5-72005

[51] Int. Cl.⁶ .................... C11D 9/00; C11D 1/18; C11D 1/32; A61K 7/06
[52] U.S. Cl. .................... 252/108; 252/541; 252/544; 252/546; 252/549; 252/550; 252/DIG. 1; 252/DIG. 6; 252/DIG. 12; 424/70.19; 424/70.22; 424/70.27; 424/401
[58] Field of Search .................... 252/108, 541, 252/544, 546, 549, 550, DIG. 1, DIG. 6, DIG. 12; 424/70.19, 70.22, 70.27, 401

[56] References Cited

U.S. PATENT DOCUMENTS

| | | | |
|---|---|---|---|
| 4,765,984 | 8/1988 | Vellekoop et al. | 424/441 |
| 5,114,717 | 5/1992 | Kuznitz et al. | 424/401 |
| 5,128,123 | 7/1992 | Brewster et al. | 424/65 |
| 5,186,855 | 2/1993 | Crudden . | |

FOREIGN PATENT DOCUMENTS

| | | | |
|---|---|---|---|
| 1617180 | 2/1971 | Germany | C11D 10/04 |
| 2262534 | 6/1993 | United Kingdom | C11D 1/16 |

Primary Examiner—F. Rollins Cross
Assistant Examiner—Patricia L. Hailey
Attorney, Agent, or Firm—Oblon, Spivak, McClelland, Maier & Neustadt

[57] ABSTRACT

A detergent composition which comprises (A) an N-acyl amino acid salt of an amino acid selected from glycine, alanine and β-alanine where the acyl group is a saturated or unsaturated fatty acid residue having 8 to 20 carbon atoms and (B) a higher fatty acid salt at a Component (A)/Component (B) weight ratio of 99.5/0.5 to 90/10, and another detergent composition derived from the above composition, which comprises further a higher alcohol and/or polyhydric alcohol. According to the present invention, properties of N-acyl amino acid salts as detergents can be improved.

6 Claims, 1 Drawing Sheet

DETERGENT COMPOSITION

TECHNICAL FIELD

This invention relates to a detergent composition which comprises an N-acyl glycine salt, an N-acyl alanine salt and/or an N-acyl β-alanine salt, together with a higher fatty acid salt, and to another detergent composition whose use feeling is improved by incorporating further a higher alcohol and/or a polyhydric alcohol.

BACKGROUND ART

N-Acyl amino acid salts are known as surface active agents generally having high safety, and, particularly, N-acyl glutamic acid salts, N-acyl sarcosine salts, N-acyl β-alanine salts, N-acyl methyl taurine salts and the like are broadly used in detergents. Other N-acyl amino acid salts have also been studied since considerably old times, and N-acyl amino acids were actually synthesized from and examined on natural amino acids and synthetically obtainable amino acids. Especially, there are a number of reports on the results of studies on N-acyl derivatives of natural amino acids.

Recently, it was reported that scum formed by the reaction of an N-acyl glycine salt, an N-acyl β-alanine salt or the like with calcium contained in city water was found to have an excellent touch (Japanese Patent Application Laid-Open (Kokai) No. Hei 4-221607). However, the N-acyl amino acid salts disclosed in this report and other natural type N-acyl amino acid salts were not sufficient in their bubble-related performances in terms of bubble retention, creaminess, lathering power and sliminess.

The object of the present invention is to provide an excellent detergent composition comprising an N-acyl amino acid salt, which is highly safe and shows quick, effective and creamy lathering and reduced slimy touch to the skin.

DISCLOSURE OF THE INVENTION

With the aim of achieving the aforementioned object, the inventors of the present invention have conducted intensive studies and found as the result that an excellent detergent composition having the aforementioned properties can be provided by jointly using a salt of a specified N-acyl amino acid and a salt of a specified higher fatty acid, or by blending further them with a specified higher alcohol and/or polyhydric alcohol, and finally accomplished the present invention on the basis of such findings.

Accordingly, the present invention relates to a detergent composition which comprises (A) an N-acyl amino acid salt of an amino acid selected from glycine, alanine and β-alanine where the acyl group is a fatty acid residue having 8 to 20 carbon atoms and (B) a higher fatty acid salt having 8 to 20 carbon atoms at a Component (A)/Component (B) weight ratio of 99.5/0.5 to 90/10, and to another detergent composition derived from the above composition, which comprises further a higher alcohol and/or polyhydric alcohol.

The present invention will be described in detail as follows.

With regard to N-acyl amino acid salts as Component (A) of the detergent composition of the present invention, the N-acyl amino acid moiety is composed of an amino acid selected from glycine, alanine and β-alanine and an acyl group which is a saturated or unsaturated fatty acid residue having 8 to 20 carbon atoms. Examples of such moiety include lauroyl glycine, cocoyl glycine, myristoyl glycine, palmitoyl glycine, stearoyl glycine, oleoyl glycine, lauroyl β-alanine, cocoyl β-alanine, myristoyl β-alanine, palmitoyl β-alanine, stearoyl β-alanine, oleoyl β-alanine, lauroyl alanine, cocoyl alanine, myristoyl alanine, palmitoyl alanine, stearoyl alanine and the like. These N-acyl amino acids may be of either optically active form or racemic form. On the other hand, examples of the base moiety include alkali metals such as sodium, potassium and the like, organic amines such as triethanolamine, diethanolamine, monoethanolamine and the like alkanol amines and basic amino acids such as lysine, ornithine, arginine and the like. These base moieties may be used as a combination of two or more, because such a combination may further improve lathering and bubble retention.

With regard to higher fatty acid salts as Component (B), examples of the higher fatty acid moiety include straight- or branched chain, saturated or unsaturated ones each having 8 to 20 carbon atoms, particularly lauric acid, myristic acid, palmitic acid, stearic acid, coconut oil fatty acids, hardened tallow fatty acids and oleic acid, while the base moiety may be selected from the aforementioned base moieties of the Component (A) N-acyl amino acid salts.

As a matter of course, the aforementioned N-acyl amino acid salts may be used alone or as a mixture of two or more. The aforementioned higher fatty acid salts can also be used in the same manner.

With regard to the ratio (by weight) of Components (A) and (B) to be comprised in the detergent composition of the present invention, bubble quality is rough, bubble retention is poor and bubble volume is insufficient when Component (A)/Component (B)=100/0. The bubble volume-increasing effect of Component (B) becomes significant and the bubble retention, creaminess of bubble quality, non-sliminess and bubble-breaking capacity become appropriate when the ratio is adjusted to the Component (A)/Component (B)=99.5/0.5, the bubble retention becomes relatively good when the Component (A)/Component (B)=98/2, and almost constant effects are obtained when the Component (A)/Component (B)=97/3. The ratio if exceeding the Component (A)/Component (B)=90/10 would cause rapid increase in the generation of unusual smells and jarring touch, thus spoiling feeling of the detergent composition when used.

Jarring touch does not occur and refreshed feeling is improved when a specified higher alcohol is jointly used in addition to the active ingredients composed of the specified N-acyl amino acid salt and the specified higher fatty acid salt.

Such higher alcohols can be straight- or branched-chain, saturated or unsaturated alcohols having 8 to 24 carbon atoms. Examples of such higher alcohols include, especially, lauryl alcohol, myristyl alcohol, stearyl alcohol, cetanol, cetostearyl alcohol and the like. As a matter of course, these higher alcohols can be used alone or jointly as a mixture of two or more, and the joint use will exert the effect in smaller amounts.

With regard to the amount of the higher alcohol (total amount when used as a mixture), 0.5 to 20% by weight based on the total amount of Components (A) and (B) may be effective, and amounts outside this range will not bear refreshed feeling.

In addition, hardening and dry-and-rough feeling of the skin and hair and stiffness of the skin can be prevented when a polyhydric alcohol is jointly used in addition to the active principle composed of the specified N-acyl amino acid salt and the specified higher fatty acid salt.

Such polyhydric alcohol to be used herein can be those alcohols which have 2 or more hydroxyl groups in one molecule. Examples include glycerol, 1,3-butylene glycol, octanediol, ethylene glycol, diethylene glycol, polyethylene glycol, propylene glycol, dipropylene glycol, polypropylene glycol, isoprene glycol, maltitol, sorbitol, pentaerythritol and the like. Of these, glycerol, 1,3-butylene glycol and propylene glycol are preferred from the view point of the use feeling and bubble volume.

Amounts of the polyhydric alcohol to be blended may be in the range of from 3 to 30% by weight, preferably from 5 to 20% by weight, of the total composition. The amount if smaller than 3% would bear no effect of its blending, and if larger than 30% would result in poor bubble quality and inferior use feeling.

With regard to the pH value of the detergent composition of the present invention, a pH value of from 6 to 10 to be provided at the time of the use of the composition is preferable from the safety point of view, and a pH value of from 6.5 to 9 is more desirable in view of the use feeling and lathering property. In consequence, the detergent composition of the present invention may be used as such if the pH value upon dissolution in water is within the above range, though it varies depending on the type of the base moiety of the N-acyl amino acid salt, but, when the value is outside the above range, a pH adjusting agent such as citric acid, carbonate or the like should have preferably been blended in advance so that the pH value is set within the range when it is used.

The detergent composition of the present invention may be made into appropriate preparation forms as detergents with no particular limitation, such as liquids, pastes, solids, powders and the like.

Also, as a matter of course, the detergent composition of the present invention can comprises such additives as commonly used in cosmetics and detergents, such as drugs, bactericides, perfumes, pigments and the like, corresponding to each application purpose, and within such a range that they do not spoil the characteristics of the present invention.

The detergent composition of the present invention shows a significant synergistic effect in terms of the bubble performance when used jointly with other anionic, nonionic and amphoteric surface active agents.

BEST MODE OF CARRYING OUT THE INVENTION

Figure 1:
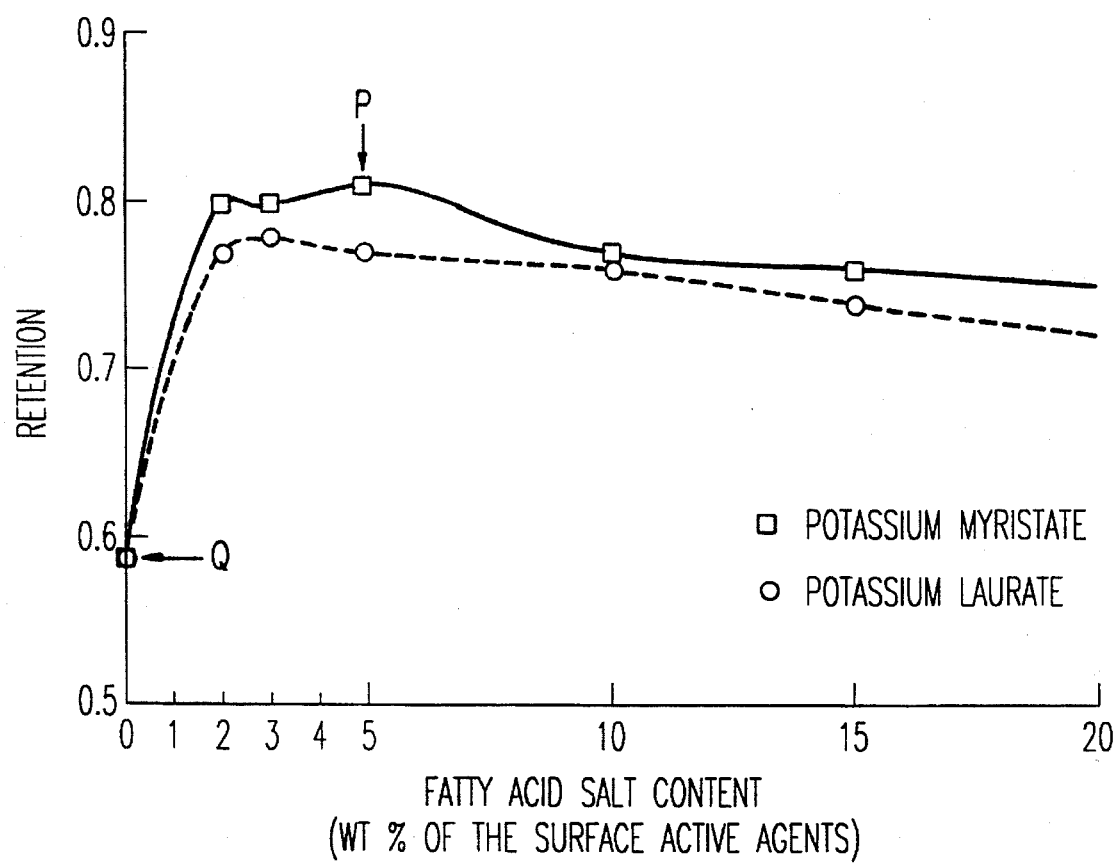
FIG. 1 shows a graph showing the results of Test Example 1.

The following examples are provided to further illustrate the present invention.

Test Example 1

N-Lauroyl glycine was synthesized in accordance with the well known Schotten-Baumann reaction, and the unreacted fatty acid and other impurities were removed from the reaction product by recrystallization to obtain highly purified N-lauroyl glycine (purity, 99.95% or more), which was subsequently neutralized with potassium hydroxide to obtain the potassium salt of N-lauroyl glycine.

Using the thus obtained potassium salt of N-lauryl glycine (Component (A)) and potassium myristate (Component (B)) in varied amounts, several aqueous solutions (pH 8.2), each containing the components in a total concentration (surfactant concentration) of 0.5% by weight, were prepared. A 50 g portion of each aqueous solution was taken and stirred in a domestic mixer "Milcer" (manufactured by Iwatani Sangyo) to examine retention of bubbles. The retention is defined based on the formula, (bubble volume (ml) 10 minutes after stirring)/(bubble volume (ml), just after stirring)×100.

Another test was carried out on the retention of bubbles completely in the same manner except that potassium laurate was used instead of potassium myristate.

The results are shown in FIG. 1. As is evident from the figure, N-acyl amino acid salt alone cannot show sufficient retention of bubbles, while the bubble retention is improved when a very small amount of a higher fatty acid salt is added to the N-acyl amino acid salt (reaching almost the maximum level by the addition of about 2% of the higher fatty acid salt).

In order to evaluate creaminess, bubbles collected just after lathering at Points P and Q in FIG. 1 were placed on a slide glass, covered with cover glasses and then observed under a fiber scope microscope "Scopeman" (manufactured by Moritex), simultaneously taking photographs. As the result, it was found that the bubbles collected at Point P where a small amount of the fatty acid salt had been added were excellent in creaminess, while the bubbles collected at Point Q where the fatty acid salt had not been added were confirmed to be unstable, because they united during the microscopic observation.

Inventive Examples 1 to 10 and Comparative Examples 1 to 7

Various types of N-acyl amino acid salts were prepared in the same manner as described in Test Example 1.

Using the thus prepared N-acyl amino acid salts and higher fatty acid salts and higher alcohols in such varied amounts as shown in Table 3, a number of aqueous solutions, each containing these components in a total concentration (surfactant concentration) of 0.5% by weight, were prepared. The pH value of each solution was found to be 7 to 8. Each of the thus prepared solutions was stirred using the domestic mixer used in Test Example 1 to examine the test items shown in Table 1.

TABLE 1

| Test item | Description |
| --- | --- |
| Bubble volume | bubble volume (ml), 5 seconds after stirring |
| Lathering rate | ⊙ : very quick, O : quick, Δ: usual, x: not sufficient |

TABLE 1-continued

| Test item | Description |
|---|---|
| Creaminess of bubbles | ⊚ : very creamy, ○ : creamy, Δ: usual, x: not sufficient |
| Retention of bubbles | retention (%) = (bubble volume (ml), 10 minutes after stirring)/bubble volume (ml), 5 seconds after stirring) × 100 |

The compositions of the present invention were evaluated as head hair and body detergents by organoleptic tests by 20 expert panelists composed of 10 females and 10 males, concerning the touch of bubbles, jarring feeling, refreshed feeling and sliminess after washing, and the smells at the time of washing as the sense of touch and feeling. The organoleptic hand-washing and hair-washing tests were carried out using test solutions prepared by diluting each of the compositions having varied blending ratios shown in Table 3 with distilled water to a surfactant concentration of 30% or 15%.

The criteria for evaluation of each test item is shown in Table 2.

TABLE 2

| Test item | Description |
|---|---|
| Touch of bubbles | ⊚ : very good, ○ : good, Δ: usual, and x: bad. |
| Jarring feeling (hands) | ⊚ : very smooth, ○ : smooth, Δ: jarring, and x: extremely jarring. |
| Jarring feeling (hair) | ⊚ : very smooth, ○ : smooth, Δ: jarring, and x: extremely jarring. |
| Refreshed feeling | ⊚ : very refreshed, ○ : refreshed, Δ: usual, and x: slimy. |
| Sliminess | ○ : not slimy, and x: slimy. |
| Smells | ⊚ : not feel at all, ○ : hardly feel, Δ: usual, and x: unpleasant smells. |

The results are shown in Table 3.

TABLE 3

| | | Inventive Examples | | | | |
|---|---|---|---|---|---|---|
| | | 1 | 2 | 3 | 4 | 5 |
| Acyl amino acid salt | Lauroyl glycine TEA | 95 | | | | |
| | Lauroyl glycine sodium | | 92 | | | |
| | Myristoyl glycine potassium | | | 90 | | |
| | Lauroyl alanine TEA | | | | 90 | |
| | Lauroyl β-alanine potassium | | | | | 90 |
| Higher fatty acid salt | Sodium laurate | | | | 10 | |
| | Potassium laurate | | 8 | | | |
| | Coconut oil fatty acid TEA | 5 | | 10 | | |
| | Potassium myristate | | | | | 10 |
| Higher alcohol | Cetanol | | | | | |
| | Lauryl alcohol | | | | | |
| Results | Bubble volume (ml) | 300 | 310 | 320 | 315 | 300 |
| | Lathering rate | ⊚ | ⊚ | ⊚ | ⊚ | ⊚ |
| | Creaminess of bubbles | ⊚ | ⊚ | ⊚ | ⊚ | ⊚ |
| | Retention of bubbles | 98 | 95 | 99 | 97 | 100 |
| | Touch of bubbles | ○ | ○ | ⊚ | ⊚ | ⊚ |
| | Sliminess | ○ | ○ | ○ | ○ | ○ |
| | Jarring feeling (hands) | ⊚ | ⊚ | ⊚ | ⊚ | ⊚ |
| | Jarring feeling (hair) | ⊚ | ⊚ | ⊚ | ⊚ | ⊚ |
| | Refreshed feeling | ○ | ○ | ○ | ○ | ○ |
| | Smells | ⊚ | ⊚ | ⊚ | ⊚ | ⊚ |

| | | Inventive Examples | | | | |
|---|---|---|---|---|---|---|
| | | 6 | 7 | 8 | 9 | 10 |
| Acyl amino acid salt | Lauroyl glycine TEA | 90 | | | | |
| | Lauroyl glycine sodium | | 92 | | | |
| | Myristoyl glycine potassium | | | 90 | | |
| | Lauroyl alanine TEA | | | | 90 | |
| | Lauroyl β-alanine potassium | | | | | 90 |
| Higher fatty acid salt | Sodium laurate | | | | 7 | |
| | Potassium laurate | | 5 | | | |
| | Coconut oil fatty acid TEA | 5 | | 7 | | |
| | Potassium myristate | | | | | 2 |
| Higher alcohol | Cetanol | 5 | 3 | | 3 | |
| | Lauryl alcohol | | | 3 | | 8 |
| Results | Bubble volume (ml) | 300 | 270 | 270 | 300 | 300 |
| | Lathering rate | ⊚ | ⊚ | ⊚ | ⊚ | ⊚ |
| | Creaminess of bubbles | ⊚ | ⊚ | ⊚ | ⊚ | ⊚ |
| | Retention of bubbles | 100 | 100 | 100 | 99 | 95 |
| | Touch of bubbles | ⊚ | ⊚ | ⊚ | ⊚ | ⊚ |
| | Sliminess | ○ | ○ | ○ | ○ | ○ |
| | Jarring feeling (hands) | ⊚ | ⊚ | ⊚ | ⊚ | ⊚ |
| | Jarring feeling (hair) | ⊚ | ⊚ | ⊚ | ⊚ | ⊚ |
| | Refreshed feeling | ⊚ | ⊚ | ⊚ | ⊚ | ⊚ |
| | Smells | ⊚ | ⊚ | ⊚ | ⊚ | ⊚ |

| Comparative Examples |
|---|

TABLE 3-continued

|  |  | 1 | 2 | 3 | 4 | 5 | 6 | 7 |
|---|---|---|---|---|---|---|---|---|
| Acyl amino acid salt | Lauroyl glycine TEA | 100 | | | | | | |
| | Lauroyl glycine sodium | | 100 | | | | | |
| | Myristoyl glycine potassium | | | 100 | | | 86 | |
| | Lauroyl alanine TEA | | | | 100 | | | |
| | Lauroyl β-alanine potassium | | | | | 100 | | |
| Higher fatty acid salt | Sodium laurate | | | | | | | 100 |
| | Potassium laurate | | | | | | 14 | |
| | Coconut oil fatty acid TEA | | | | | | | |
| | Potassium myristate | | | | | | | |
| Higher alcohol | Cetanol | | | | | | | |
| | Lauryl alcohol | | | | | | | |
| Results | Bubble volume (ml) | 270 | 270 | 270 | 240 | 270 | 270 | 270 |
| | Lathering rate | x | x | x | x | x | ◉ | ◉ |
| | Creaminess of bubbles | x | x | Δ | x | x | ◉ | ◉ |
| | Retention of bubbles (%) | 60 | 68 | 74 | 75 | 65 | 95 | 60 |
| | Touch of bubbles | Δ | Δ | Δ | Δ | Δ | ◉ | ◉ |
| | Sliminess | x | x | x | x | x | ○ | ○ |
| | Jarring feeling (hands) | ◉ | ◉ | ◉ | ◉ | ◉ | Δ | x |
| | Jarring feeling (hair) | ◉ | ◉ | ◉ | ◉ | ◉ | Δ | x |
| | Refreshed feeling | Δ | Δ | Δ | Δ | Δ | ○ | ◉ |
| | Smells | ○ | ○ | ○ | ○ | ○ | x | x |

*TEA = triethanolamine

Inventive Examples 11 to 21 and Comparative Examples 8 to 18

In order to examine the effects of the joint use of the detergent composition of the present invention with other surface active agents, physical property measurement and organoleptic tests were carried out in the same manner as described in the preceding inventive examples. In this case, each aqueous solution was prepared by weighing the respective surface active agents in the amount (g) shown in Table 4 and adding purified water to the weighed agents in such an amount that the total weight was adjusted to 100 g. The pH value of each solution was found to be 7 to 8.

The results are shown in Table 4.

TABLE 4

|  |  | Inventive Examples | | | | | |
|---|---|---|---|---|---|---|---|
|  |  | 11 | 12 | 13 | 14 | 15 | 16 |
| Acyl amino acid salt | Cocoyl glycine TEA | 5 | 10 | 10 | | | 20 |
| | Cocoyl glycine potassium | | | | 20 | 20 | |
| | Cocoyl glycine sodium | | | | | | |
| | Lauroyl glycine sodium | | | | | | |
| | Cocoyl alanine TEA | | | | | | |
| | Cocoyl β-alanine TEA | | | | | | |
| Higher fatty acid salt | Coconut oil fatty acid potassium | | 0.5 | 0.5 | | | |
| | Soap base | | | | | | |
| | Coconut oil fatty acid TEA | 0.5 | | | 0.5 | 1 | 2.5 |
| | Potassium myristate | | | | | | |
| Higher alcohol | Cetanol | | | | 0.5 | | 3 |
| | Lauryl alcohol | | | | | 0.5 | |
| Anionic surface active agent | Lauroyl methyltaurine sodium | 5 | | | | | |
| | Monolauryl phosphate TEA | | | | 2 | | 5 |
| | Sodium cocoyl isethionate | | | | | | |
| Amphoteric surface active agent | Lauryl dimethylaminoacetic acid betaine | 8 | | | | 10 | |
| | 2-Lauryl-N-carboxymethyl-N-hydroxyethylimidazolinium betaine | | 3 | | | | |
| | Coconut oil fatty acid amide propyldimethylamino acetic acid betaine | | | 3 | | | |
| | Lauryl dimethylamino-2-hydroxypropyl sulfobetaine | | | | 5 | | |
| Nonionic surface active agent | Coconut oil fatty acid diethanolamide | 2 | 2 | 2 | | | 3 |
| | Lauryl polyglycoside | | | | 1 | | |
| Results | Bubble volume (ml) | 295 | 290 | 290 | 298 | 280 | 310 |
| | Lathering rate | ◉ | ◉ | ◉ | ○ | ◉ | ◉ |
| | Creaminess of bubbles | ◉ | ◉ | ◉ | ◉ | ◉ | ◉ |
| | Retention of bubbles (%) | 88 | 99 | 99 | 99 | 97 | 99 |

TABLE 4-continued

|  |  |  |  |  |  |  |  |
|---|---|---|---|---|---|---|---|
|  | Touch of bubbles | ○ | ◎ | ◎ | ◎ | ◎ | ◎ |
|  | Jarring feeling (hands) | ◎ | ◎ | ◎ | ◎ | ◎ | ◎ |
|  | Jarring feeling (hair) | ◎ | ◎ | ◎ | ◎ | ◎ | ◎ |
|  | Sliminess | ○ | ○ | ○ | ○ | ○ | ○ |
|  | Refreshed feeling | ○ | ○ | ○ | ◎ | ◎ | ◎ |
|  | Smells | ○ | ○ | ○ | ◎ | ○ | ○ |

|  |  | Inventive Examples ||||| 
|---|---|---|---|---|---|---|
|  |  | 17 | 18 | 19 | 20 | 21 |
| Acyl amino acid salt | Cocoyl glycine TEA |  |  |  |  |  |
|  | Cocoyl glycine potassium |  |  |  |  |  |
|  | Cocoyl glycine sodium |  |  |  |  |  |
|  | Lauroyl glycine sodium | 20 | 20 |  |  |  |
|  | Cocoyl alanine TEA |  |  | 25 |  |  |
|  | Cocoyl β-alanine TEA |  |  |  | 25 | 20 |
| Higher fatty acid salt | Coconut oil fatty acid potassium |  |  |  |  |  |
|  | Soap base | 1 |  |  |  |  |
|  | Coconut oil fatty acid TEA |  |  |  | 2.5 |  |
|  | Potassium myristate |  | 1 | 2.5 |  | 2 |
| Higher alcohol | Cetanol |  |  |  |  |  |
|  | Lauryl alcohol |  |  |  | 3 |  |
| Anionic surface active agent | Lauroyl methyltaurine sodium |  |  |  |  |  |
|  | Monolauryl phosphate TEA |  |  |  |  |  |
|  | Sodium cocoyl isethionate | 5 |  |  |  |  |
| Ampho- teric surface active agent | Lauryl dimethylaminoacetic acid betaine |  |  |  |  |  |
|  | 2-Lauryl-N-carboxymethyl-N-hydroxyethylimidazolinium betaine |  |  |  |  | 10 |
|  | Coconut oil fatty acid amide propyldimethylamino acetic acid betaine |  |  |  |  |  |
|  | Lauryl dimethylamino-2-hydroxypropyl sulfobetaine |  |  |  |  |  |
| Nonionic surface active agent | Coconut oil fatty acid diethanolamide |  |  | 5 |  | 5 |
|  | Lauryl polyglycoside |  | 10 |  | 2.5 |  |
| Results | Bubble volume (ml) | 300 | 270 | 270 | 300 | 290 |
|  | Lathering rate | ◎ | ◎ | ◎ | ◎ | ◎ |
|  | Creaminess of bubbles | ◎ | ◎ | ◎ | ◎ | ◎ |
|  | Retention of bubbles (%) | 100 | 100 | 100 | 99 | 95 |
|  | Touch of bubbles | ◎ | ◎ | ◎ | ◎ | ◎ |
|  | Jarring feeling (hands) | ◎ | ◎ | ◎ | ◎ | ◎ |
|  | Jarring feeling (hair) | ◎ | ◎ | ◎ | ◎ | ◎ |
|  | Sliminess | ○ | ○ | ○ | ○ | ○ |
|  | Refreshed feeling | ○ | ○ | ◎ | ○ | ○ |
|  | Smells | ○ | ○ | ○ | ○ | ○ |

|  |  | Comparative Examples |||||| 
|---|---|---|---|---|---|---|---|
|  |  | 8 | 9 | 10 | 11 | 12 | 13 |
| Acyl amino acid salt | Cocoyl glycine TEA | 5 |  |  |  |  |  |
|  | Cocoyl glycine potassium |  |  |  |  |  |  |
|  | Cocoyl glycine sodium |  |  |  |  |  |  |
|  | Lauroyl glycine sodium |  |  | 20 | 20 | 20 |  |
|  | Cocoyl alanine TEA |  | 7 |  |  |  | 25 |
|  | Cocoyl β-alanine TEA |  |  |  |  |  |  |
| Higher fatty acid salt | Coconut oil fatty acid potassium |  |  |  |  |  |  |
|  | Soap base |  |  |  |  |  |  |
|  | Coconut oil fatty acid TEA |  |  |  |  |  |  |
|  | Potassium myristate |  |  |  |  |  |  |
| Higher alcohol | Cetanol |  | 0.5 |  |  |  |  |
|  | Lauryl alcohol |  |  |  |  |  |  |
| Anionic surface active agent | Lauroyl methyltaurine sodium | 5 |  |  |  |  |  |
|  | Monolauryl phosphate TEA |  | 2 |  |  |  |  |
|  | Sodium cocoyl isethionate |  |  |  | 5 |  |  |
| Ampho- teric surface active agent | Lauryl dimethylaminoacetic acid betaine | 8 |  |  |  |  |  |
|  | 2-Lauryl-N-carboxymethyl-N-hydroxyethylimidazolinium betaine |  |  |  |  |  |  |

TABLE 4-continued

|  |  |  |  |  |  |  |  |
|---|---|---|---|---|---|---|---|
|  | Coconut oil fatty acid amide propyldimethylamino acetic acid betaine |  |  |  |  |  |  |
|  | Lauryl dimethylamino-2-hydroxypropyl sulfobetaine |  | 5 |  |  |  |  |
| Nonionic surface active agent | Coconut oil fatty acid diethanolamide | 2 |  |  |  |  | 5 |
|  | Lauryl polyglycoside |  |  | 1 | 10 | 10 |  |
| Results | Bubble volume (ml) | 270 | 240 | 230 | 240 | 250 | 235 |
|  | Lathering rate | ⊙ | Δ | Δ | Δ | Δ | Δ |
|  | Creaminess of bubbles | x | x | x | x | x | x |
|  | Retention of bubbles (%) | 60 | 64 | 63 | 67 | 68 | 64 |
|  | Touch of bubbles | Δ | Δ | Δ | Δ | Δ | Δ |
|  | Jarring feeling (hands) | ○ | x | ⊙ | ⊙ | ⊙ | ⊙ |
|  | Jarring feeling (hair) | ⊙ | ⊙ | x | Δ | Δ | ○ |
|  | Sliminess | x | x | x | x | x | x |
|  | Refreshed feeling | x | x | x | x | x | x |
|  | Smells | ○ | ○ | ○ | ○ | ○ | ○ |

|  |  | Comparative Examples |  |  |  |  |
|---|---|---|---|---|---|---|
|  |  | 14 | 15 | 16 | 17 | 181 |
| Acyl amino acid salt | Cocoyl glycine TEA |  |  | 85 |  |  |
|  | Cocoyl glycine potassium |  |  |  | 80 |  |
|  | Cocoyl glycine sodium |  |  |  |  | 85 |
|  | Lauroyl glycine sodium |  |  |  |  |  |
|  | Cocoyl alanine TEA |  |  |  |  |  |
|  | Cocoyl β-alanine TEA | 25 | 20 |  |  |  |
| Higher fatty acid salt | Coconut oil fatty acid potassium |  |  |  | 20 |  |
|  | Soap base |  |  |  |  |  |
|  | Coconut oil fatty acid TEA |  |  | 15 |  |  |
|  | Potassium myristate |  |  |  |  | 13 |
| Higher alcohol | Cetanol |  |  |  |  |  |
|  | Lauryl alcohol |  |  |  |  |  |
| Anionic surface active agent | Lauroyl methyltaurine sodium |  |  |  |  |  |
|  | Monolauryl phosphate TEA |  |  |  |  |  |
|  | Sodium cocoyl isethionate |  |  |  |  |  |
| Amphoteric surface active agent | Lauryl dimethylaminoacetic acid betaine |  |  |  |  |  |
|  | 2-Lauryl-N-carboxymethyl-N-hydroxyethylimidazolinium betaine |  | 10 |  |  |  |
|  | Coconut oil fatty acid amide propyldimethylamino acetic acid betaine |  |  |  |  |  |
|  | Lauryl dimethylamino-2-hydroxypropyl sulfobetaine |  |  |  |  |  |
| Nonionic surface active agent | Coconut oil fatty acid diethanolamide |  | 5 |  |  |  |
|  | Lauryl polyglycoside | 5 |  | 5 |  |  |
| Results | Bubble volume (ml) | 260 | 230 | 300 | 300 | 300 |
|  | Lathering rate | Δ | Δ | ⊙ | ⊙ | ⊙ |
|  | Creaminess of bubbles | x | x | ⊙ | ⊙ | ⊙ |
|  | Retention of bubbles (%) | 68 | 63 | 99 | 98 | 97 |
|  | Touch of bubbles | Δ | Δ | ⊙ | ⊙ | ⊙ |
|  | Jarring feeling (hands) | ⊙ | ⊙ | x | x | x |
|  | Jarring feeling (hair) | ⊙ | ○ | x | x | x |
|  | Sliminess | x | x | ○ | ○ | ○ |
|  | Refreshed feeling | x | x | ⊙ | ⊙ | ⊙ |
|  | Smells | ○ | ○ | x | x | x |

Inventive Examples 22 and 23 and Comparative Example 19

In order to examine the effects of pH on the detergent composition of the present invention, detergent compositions of the compositions shown in Table 5 were prepared and their bubble volumes and used feelings were evaluated. The pH value of each detergent composition was adjusted with potassium hydroxide or citric acid.

TABLE 5

|  | Comparative Example | Inventive Examples | |
|---|---|---|---|
|  | 19 | 22 | 23 |
| Potassium lauroyl glycinate | 25 | 25 | 25 |
| Potassium laurate | 1.5 | 1.5 | 1.5 |
| Water | balance | balance | balance |
| pH | 5.5 | 6.5 | 9.0 |
| Bubble volume (ml) | 180 | 280 | 320 |
| Stiffness | x | ○ | ○ |
| Retention of bubbles | x | ○ | ○ |

Used feelings, namely stiffness and bubble retention when the side of the forearm was washed with a nylon towel using each of the above compositions, were evaluated based on the following criteria by 20 expert panelists consisting of 10 females and 10 males.

Stiffness ◉: completely no stiffness, ○: no stiffness, Δ: usual, and x: stiffen.

Bubble retention ◉: very good, ○: good, Δ: usual, and x: not enough.

Inventive Examples 24 to 26

In order to examine the effects of the addition of polyhydric alcohols to the detergent composition of the present invention, detergent compositions of the compositions shown in Table 6 were prepared and their bubble volumes and used feelings were evaluated.

TABLE 6

|  | Inventive Examples | | |
|---|---|---|---|
|  | 24 | 25 | 26 |
| Potassium lauroyl glycinate | 25 | 25 | 25 |
| Potassium laurate | 1.5 | 1.5 | 1.5 |
| Glycerol | 5 | 25 | 5 |
| Propylene glycol |  |  | 10 |
| 1,3-Butylene glycol |  |  | 5 |
| Water | balance | balance | balance |
| pH | 8.2 | 8.2 | 8.2 |
| Bubble volume (ml) | 310 | 305 | 305 |
| Stiffness | ◉ | ◉ | ◉ |
| Retention of bubbles | ○ | ○ | ○ |

Inventive Examples 27 to 31

In order to examine the effects of N-acyl amino acid salts on the detergent composition of the present invention, detergent compositions of the compositions shown in Table 7 were prepared and their bubble volumes and used feelings were evaluated. The pH value of each of the detergent compositions was adjusted with 25% aqueous solutions of the respective bases mixed at the mixing ratios shown in the table.

TABLE 7

|  | Inventive Examples | | | | |
|---|---|---|---|---|---|
|  | 27 | 28 | 29 | 30 | 31 |
| Lauroyl glycine | 25 | 25 | 25 | 25 | 25 |
| Lauric acid | 1.5 | 1.5 | 1.5 | 1.5 | 1.5 |
| Base |  |  |  |  |  |
| KOH | 90 | 10 |  | 10 | 90 |
| NaOH | 10 | 90 | 25 |  |  |
| TEA |  |  | 75 | 90 | 10 |
| Glycerol |  |  |  | 5 | 10 |
| Propylene glycol |  |  |  |  | 10 |
| 1,3-Butylene glycol |  |  | 2 |  |  |
| Water | balance | balance | balance | balance | balance |
| pH | 8.5 | 7.8 | 7.1 | 6.8 | 8.0 |
| Bubble volume (ml) | 315 | 310 | 300 | 305 | 310 |
| Stiffness | ○ | ○ | ○ | ◉ | ◉ |
| Bubble retention | ◉ | ◉ | ◉ | ◉ | ◉ |

Inventive Example 32

Detergent compositions shown in the following Tables 8 to 16 were prepared in the usual way based on various formulations of materials shown in the tables.

TABLE 8

| Body shampoo | |
|---|---|
| N-Coconut oil fatty acid acyl glycine potassium salt | 20 g |
| Coconut oil fatty acid sodium salt | 2 |
| Coconut oil fatty acid diethanolamide | 5 |
| Cetanol | 1 |
| Sodium chloride | 2 |
| Methylparaben | 0.2 |
| Sodium benzoate | 0.2 |
| Sodium citrate | 0.5 |
| Purified water | balance |
| Total | 100 g |
| pH 8.2 | |

TABLE 9

| Cleansing foam | |
|---|---|
| N-Coconut oil fatty acid acyl DL-alanine sodium salt | 20 g |
| Potassium myristate | 2 |
| Propylene glycol | 4 |
| Cetostearyl alcohol | 3 |
| Coconut oil fatty acid diethanolamide | 6 |
| Sodium chloride | 2 |
| Sodium sulfate | 4 |
| Methylparaben | 0.2 |
| Sodium benzoate | 0.2 |
| Sodium citrate | 0.5 |
| Purified water | balance |
| Total | 100 g |
| pH 8.7 | |

TABLE 10

| Hair shampoo | |
|---|---|
| Lauroyl glycine sodium salt | 5 g |
| Sodium laurate | 0.4 |
| Sodium polyoxyethylene lauryl sulfate | 6 |
| 1,3-Butylene glycol | 4 |
| Coconut oil fatty acid diethanolamide | 7 |

TABLE 10-continued

Hair shampoo

| | |
|---|---|
| Sodium chloride | 2 |
| Sodium edetate | 0.1 |
| Purified water | balance |
| Total | 100 g |
| pH 7.5 | |

TABLE 11

Hair shampoo

| | |
|---|---|
| Lauryl dimethylaminoacetic acid betaine | 10 g |
| Myristoyl glycine TEA | 10 |
| Myristoyl glycine lysine | 7 |
| Palmitic acid TEA | 0.7 |
| Glycerol | 2.5 |
| 1,3-Butylene glycol | 2 |
| Coconut oil fatty acid diethanolamide | 7 |
| Sodium chloride | 2 |
| Sodium edetate | 0.1 |
| Purified water | balance |
| Total | 100 g |
| pH 7.2 | |

TABLE 12

Hair shampoo

| | |
|---|---|
| Coconut oil fatty acid amidopropyl dimethylamino acetic acid betaine | 10 g |
| Palm kernel oil fatty acid glycine TEA | 5 |
| Stearic acid lysine salt | 0.2 |
| Lauric acid diethanolamide | 4 |
| Myristyl alcohol | 1 |
| Sodium chloride | 2 |
| 1-Menthol | 0.1 |
| Purified water | balance |
| Total | 100 g |
| pH 7.4 | |

TABLE 13

Hair shampoo

| | |
|---|---|
| Lauryl dimethylamino-2-hydroxypropyl sulfobetaine | 12 g |
| Myristoyl-β-alanine TEA | 6 |
| Myristic acid lysine salt | 0.1 |
| Glycerol | 5 |
| Lauric acid diethanolamide | 4 |
| Sodium chloride | 2 |
| Herb extract | 0.1 |
| Purified water | balance |
| Total | 100 g |
| pH 7.0 | |

TABLE 14

Syndet bar

| | |
|---|---|
| Coconut oil isethionic acid sodium salt | 60 g |
| N-Palm kernel oil fatty acid acyl β-alanine potassium salt | 25 g |
| Coconut oil fatty acid lysine salt | 2 |
| Isoprene glycol | 5 |
| Lauryl glycoside | 4 |
| Cationized cellulose | 0.2 |
| Trimethylaminoacetic acid betaine | 2 |

TABLE 14-continued

Syndet bar

| | |
|---|---|
| Sodium sulfite | 0.05 |
| Sodium thiosulfate | 0.1 |
| 1-Hydroxyethylidene-1,1-diphosphonic acid Na salt | 0.1 |
| Purified water | balance |
| Total | 100 g |
| pH 7.9 | |

TABLE 15

Cleansing liquid

| | |
|---|---|
| Palm kernel oil fatty acid glycine lysine salt | 15 g |
| Palm kernel oil fatty acid | 1 |
| Sodium laurylsulfate | 5 |
| Trehalose | 5 |
| Sodium polyacrylate | 2 |
| PCA soda | 0.1 |
| Purified water | balance |
| Total | 100 g |
| pH 7.2 | |

TABLE 16

Aerosol detergent

| | |
|---|---|
| Coconut oil glycine arginine salt | 20 g |
| Coconut oil fatty acid arginine salt | 1.5 |
| Lauric acid TEA | 0.5 |
| Glycerol | 4.5 |
| Sodium polyglutamate | 0.1 |
| Coconut oil fatty acid ethanolamide | 3 |
| Sodium chloride | 2 |
| Butylparaben | 0.2 |
| Sodium benzoate | 0.2 |
| Sodium citrate | 0.5 |
| Propellant | 10 |
| Purified water | balance |
| Total | 100 g |
| pH 7.6 | |

Industrial Applicability

The considerable improvement of the properties of N-acyl amino acid salts as detergents thus achieved by the present invention has rendered possible easy provision of excellent detergent compositions.

We claim:

1. A detergent composition which comprises Component (A) an N-acyl amino acid salt of an amino acid selected from glycine, alanine and β-alanine where the acyl group is a fatty acid residue having 8 to 20 carbon atoms and Component (B) a higher fatty acid salt having 8 to 20 carbon atoms at a Component (A)/Component (B) weight ratio of 99.5/0.5 to 90/10.

2. The detergent composition of claim 1 which comprises, in addition to said Components (A) and (B), further a higher alcohol having 8 to 24 carbon atoms in an amount of from 0.5 to 20% by weight based on the total amount of the Components (A) and (B).

3. The detergent composition of claim 1 which has a pH value of from 6.5 to 9.

4. The detergent composition of claim 1 which comprises further a polyhydric alcohol.

5. The detergent composition of claim 1 which said

N-acyl amino acid salt is a combination of at least two salts selected from the group consisting of the sodium, potassium, triethanolamine, diethanolamine, monoethanolamine, lysine, ornithine and arginine salts.

6. The detergent composition of claim 1 which comprises one or more surface active agents selected from anionic (excluding the Component (A) N-acyl amino acid salts), nonionic and amphoteric surface active agents.

* * * * *